United States Patent [19]

Jagt et al.

[11] Patent Number: 5,026,726
[45] Date of Patent: Jun. 25, 1991

[54] GOSSYLIC IMINOLACTONES AND GOSSYLIC LACTONES AND THEIR ANTI-VIRAL ACTIVITIES

[75] Inventors: David L. Jagt, Albuquerque; Robert E. Royer, Bosque Farms, both of N. Mex.

[73] Assignee: The University of New Mexico, Albuqueque, N. Mex.

[21] Appl. No.: 448,432

[22] Filed: Dec. 11, 1989

[51] Int. Cl.$^5$ .................... A61K 31/34; C07D 307/92
[52] U.S. Cl. ..................... 514/468; 549/299; 549/460; 514/520; 514/569; 514/532; 558/415; 558/423; 568/328; 568/440; 564/180; 560/56; 562/467

[58] Field of Search ................ 549/299, 460; 514/468

[56] References Cited

U.S. PATENT DOCUMENTS 4,297,341 10/1981 Waller et al. ................. 514/700
4,381,298 4/1983 Coulson ........................ 514/171
4,806,568 2/1989 Vander Jagt et al. ........... 514/522

OTHER PUBLICATIONS

Sood et al., CA 98:104271d.
Seshadri et al., CA 86:27674 K.
Arustamyah et al., CA 95:61040W.
Mahoney et al., CA 111:7627d.
Manmade et al., Experiencia 39:1276 (1983).
The National Coordinating Groups on Male Fertility, Chinese Med J. 4:417-428 (1978).
Dorsett et al., J. Pharm. Sci. 64:1073 (1975).
Radloff, R. J. et al., Pharmacological Res. Comm. 18:1063-1073 (1986).
Gallo, R. C. et al., Science 220:865-867 (1983).
Fischl et al., New Eng. J. Med. 317:185-191 (1987).
Richman, D. D. et al., New Eng. J. Med. 317, 192-197 (1987).
Lardner, B. A. et al., Science 243:1731-1734 (1989).
Barre-Sinoussi, F. et al., Science 220:868-871 (1983).
Vander Jagt, et al., "A Derivative of Gossypol Retains Antimalarial Activity" (1984).
"Barre-Sinoussi et al., Isolation of a T-Lymphotropic Retrovirus from a Patient at Risk for Acquired Immune Deficiency Syndrome" Science, vol. 220, pp. 868-871.
Wichmann et al., Inhibiting Herpes Simplex Virus Type 2 Infection Human Epithelial Cells by Gossypol, a Potent Spermicidal and Contraceptive Agent, Am. J. Obst., vol. 112, pp. 593 ∝ 594.
Royer et al., "Binding of Gossypol Derivatives to Human Serum Albumin", J. of Pharm. Sciences, vol. 77, No. 3, pp. 237-240.
Royer et al., "Biologically Active Derivatives of Gossypol: Synthesis and Antimalarial Activities of Peri--Acylated Gossylic Nitriles", Am. Chem. Soc., 1986, pp. 1799-1801.

*Primary Examiner*—Jane T. Fan
*Attorney, Agent, or Firm*—Lowe, Price, LeBlanc, Becker & Shur

[57] ABSTRACT

A compound of the chemical formula

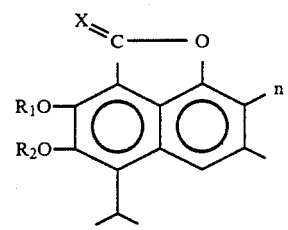

wherein n is 1 or 2, X is NH and O, and $R_1$ and $R_2$ are H, ($C_1$-$C_{12}$) alkyl, ($C_2$-$C_{12}$)alkenyl, ($C_2$-$C_{12}$)alkynyl, ($C_2$-$C_{12}$)acyl, ($C_6$-$C_{12}$)aryl or ($C_7$-$C_{21}$)alkylaryl, salts thereof and a composition thereof. In vivo and in vitro methods of inhibiting the growth of a virus relying on the effect of the above compound. In vitro and in vivo methods of inhibiting the growth of the HIV-1 virus comprising administering a compound of the formula (Abstract continued on next page.)

-continued

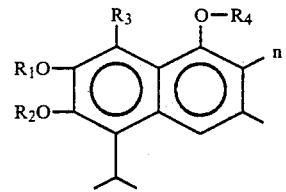

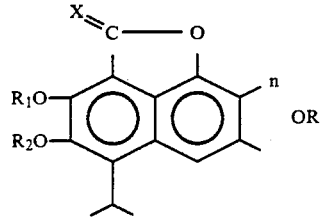 OR wherein n is 1 or 2, X is NH or O, and $R_1$ and $R_2$ are independently of one another H, $(C_1-C_{12})$alkyl, $(C_2-C_{12})$alkenyl, $(C_2-C_{12})$alkynyl, $(C_2-C_{12})$acyl, $(C_6-C_{12})$aryl or $(C_7-C_{21})$alkylaryl, $R^3$ is C≡N or $COR^5$, wherein $R^5$ is selected from the group consisting of H, $(C_1-C_{12})$ alkyl, alenyl or alkynyl, HO, $NH_2$ and $(C_2-C_{12})$ alkoxy, and $R^4$ is selected from the group consisting of $(C_1-C_{12})$ alkyl, alkenyl or alkynyl and $(C_2-C_{12})$ acyl, and pharmaceutically-acceptable salts thereof, for a period of time effective to attain the desired result to a subject or to cell suspensions infected with the virus.

12 Claims, 2 Drawing Sheets

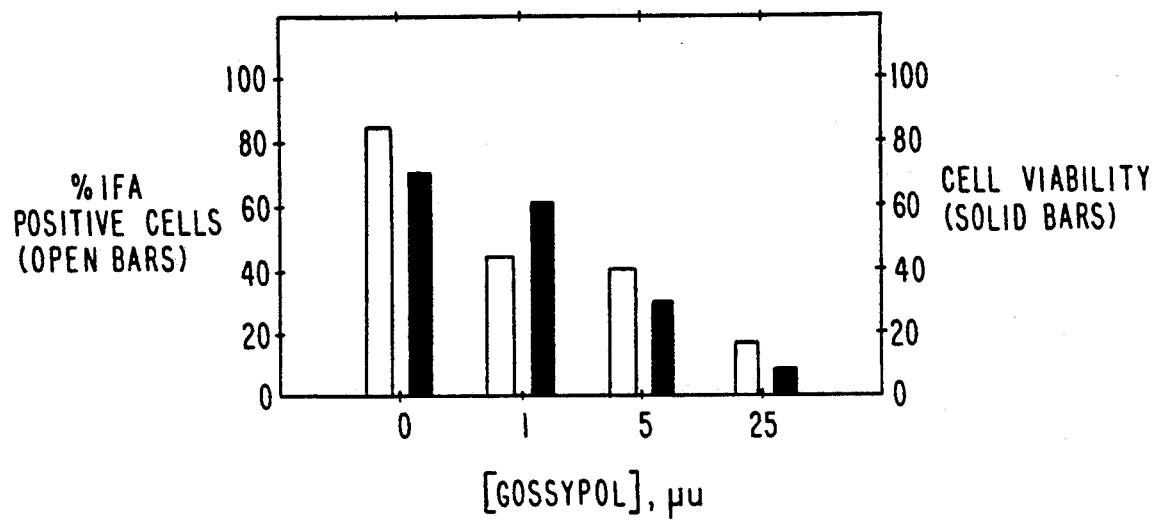
Figure 1-A
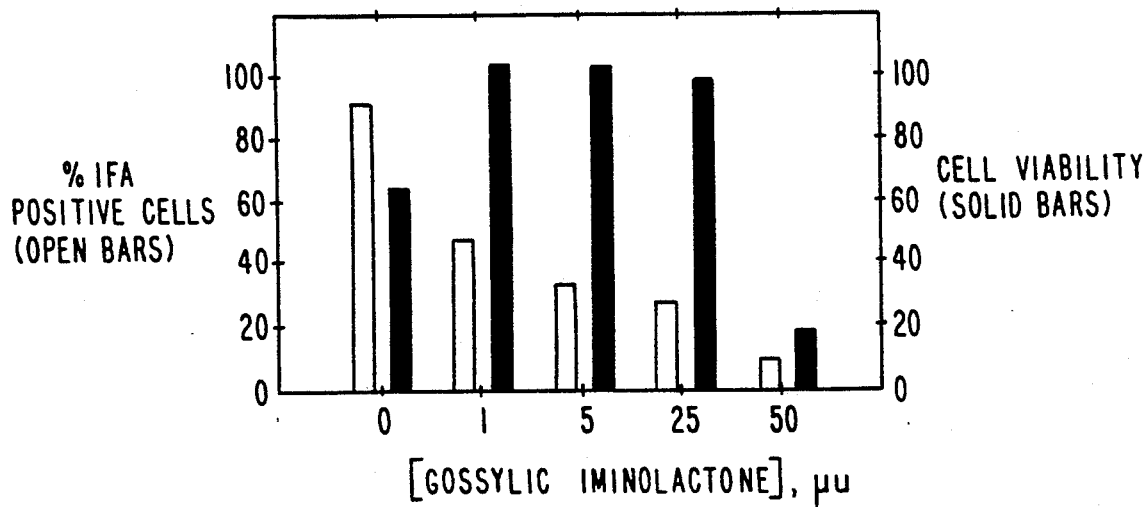
Figure 1-B

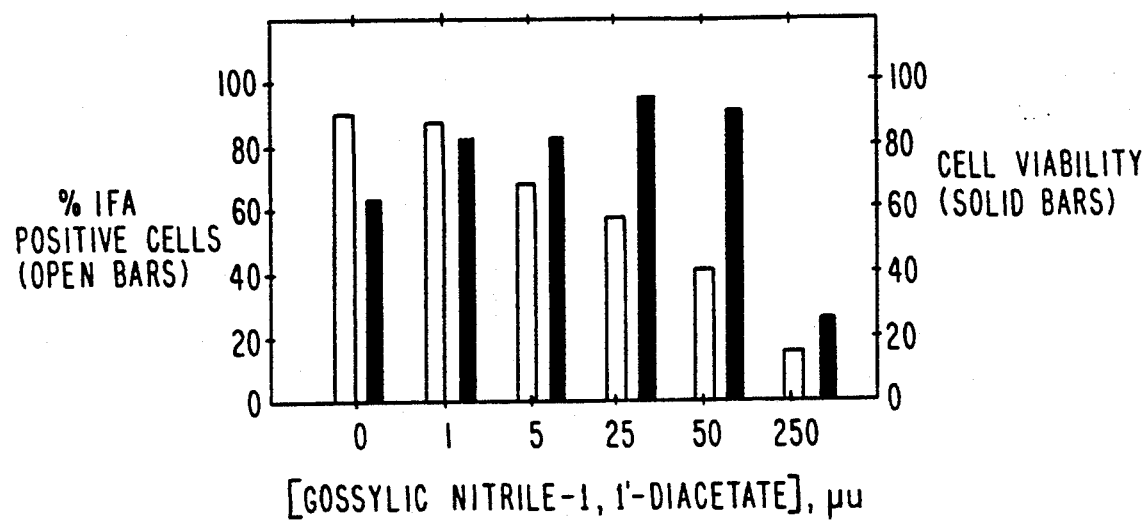
Figure 1-C
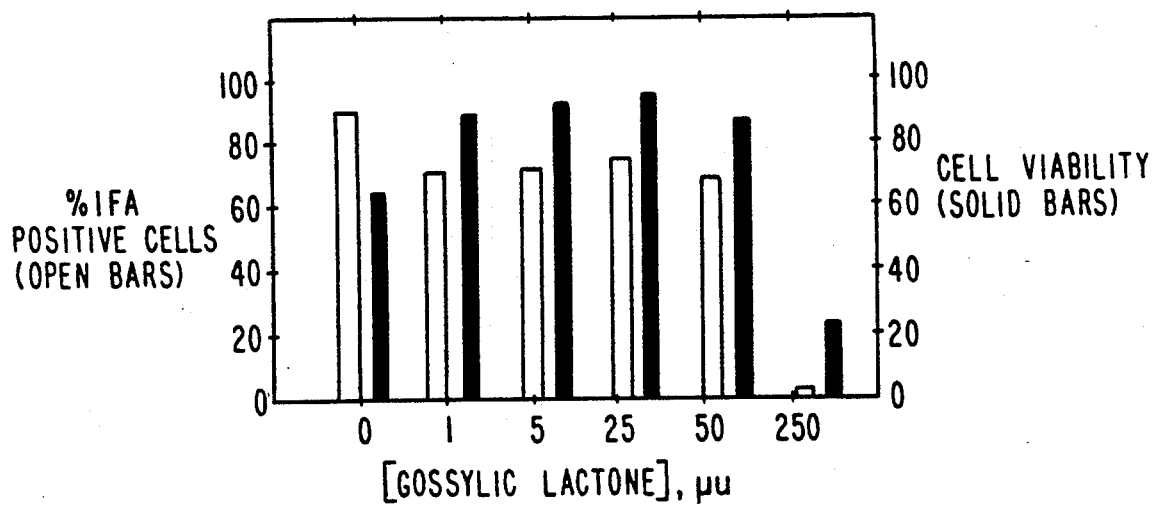
Figure 1-D

GOSSYLIC IMINOLACTONES AND GOSSYLIC LACTONES AND THEIR ANTI-VIRAL ACTIVITIES

TECHNICAL FIELD

This invention relates to novel gossypol derivatives which have been shown to have broad anti-viral activities. In addition, previously known gossypol derivatives have also been shown to be active against the HIV-1 virus.

BACKGROUND OF THE INVENTION

Gossypol is a polyphenolic triterpene derivative having the chemical formula

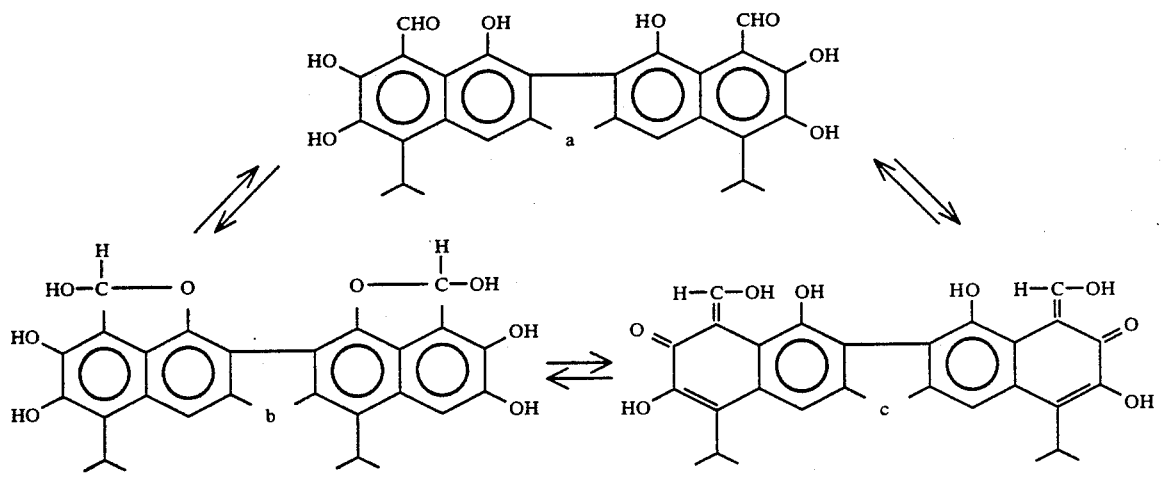

wherein b and c are tautomers of the aldehyde a. Gossypol exists primarily as the aldehyde form in nonpolar solvents and is represented as such throughout the specification and claims. Gossypol is found in certain types of cotton plants and is the main toxic material found therein. As such, it has limited the use of cottonseed meal as a source of dietary protein for monogastric animals including man. Gossypol, however, exhibits a number of useful biological properties which render it of interest for medical purposes.

Gossypol was studied for its effects on infertility and as a vaginal spermicide in China because of the discovery that the use of cotton-seed oil in cooking induced infertility in men (National Coordinating Groups on Male Fertility, Chinese Med. J. 4(6): 417-428 (1978)). This feature was used to attempt to produce a male contraceptive using gossypol as the active agent (U.S. Pat. No. 4,381,298) as well as a vaginal spermicide (U.S. Pat. No. 4,297,341). Similar properties have been attributed to the compound hemigossypol. (Manmade, et al., Experiencia 39: 1276 (1983)).

Gossypol has also been shown to have antiviral properties, being capable of inactivating parainfluenza type 3 and herpes simplex viruses (Dorsett et al., J. Pharm. Sci. 64: 1073 (1975)). Antiparasitic activity has also been found to be associated with gossypol.

Growth of both *Trypanosoma cruzi* (Montamat et al., Science 218: 288 (1982)) and *Plasmodium falcicarum* (Heidrich et al., IRCS Med. Sci 11: 304 (1983)) are inhibited by gossypol. Any practical applications of these properties have been prevented though by the toxicity and unpleasant side effects produced by gossypol.

A considerable body of research suggests that the toxicity of this compound may be related to reactions of the aldehyde groups in the molecule. The removal of its aldehyde groups, however, may lead to a reduction in toxicity as well as biological activity. It is thus difficult to predict whether any gossypol molecule without the aldehydes will exhibit activity similar to the natural molecule. It is also substantially unpredictable as to what, if any, substituent groups might be used as appropriate replacements for the aldehyde groups which might mimic the biological activity of the original compound.

U.S. Pat. No. 4,806,568 by the present inventors discloses a series of gossypol derivatives having activities similar to those of the parent compound, although lacking free aldehyde moieties. These compounds were shown to be useful in the treatment of malaria and some viral diseases, such as those caused by herpes simplex virus.

The natural product gossypol and known gossypol derivatives were found to exhibit antiviral activities against herpes simplex virus type II (Radloff, R. J. et al, Pharmacological Res. Comm. 18: 1063-1073 (1986)). This, as well as other reports of antiviral properties of gossypol, suggest that the antiviral activities of gossypol and derivatives result from the effects of these drugs on the viral envelope. This conclusion is based upon the observation that these known drugs do not inhibit the replication of naked viruses. In addition, these known drugs are active against both RNA and DNA enveloped viruses.

Acquired immunodeficiency syndrome (AIDS) is a fatal disease that results from infection by human immunodeficiency virus (HIV) (Gallo, R. C., et al, Science 220: 865-867 (1983)); Barre-Sinoussi, F. et al, Science 220: 868-871 (1983)). At present, the only approved drug for use against HIV infections is 3'-azido-2',3'-dideoxythymidine (AZT, zidovudine) (Fischl, M. A., et al, New Eng. J. Med. 317: 185-191 (1987)). Its hematologic toxicity limits, and in some cases precludes, the use of AZT in many HIV-infected patients (Richman, D. D. et al, New Eng. J. Med. 317, 192-197 (1987)). Moreover, it has been recently reported that the HIV virus may develop resistance to AZT after prolonged exposure (Larder, B. A., et al, Science 243: 1731-1734 (1989)) AZT is an inhibitor of the enzyme reverse transcriptase (RT), a key viral enzyme. It is believed that AZT exerts its effect on HIV by interfering with the RT enzyme.

In view of the AZT toxicity and also the resistance shown by patients to AZT, there is a critical need for new antiviral drugs directed against HIV, particularly for new drugs that do not share the same mechanism as AZT.

DISCLOSURE OF THE INVENTION

This invention relates to a compound of the chemical formula

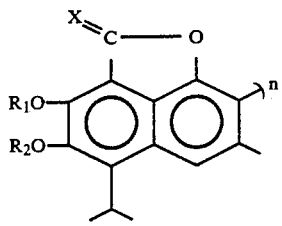

wherein
n is 1 or 2;
X is selected from the group consisting of NH and O; and
$R_1$ and $R_2$ are independently of one another H, $(C_1-C_{12})$alkyl $(C_2-C_{12})$alkenyl, $(C_2-C_{12})$alkynyl, $(C_2-C_{12})$acyl, $(C_6-C_{12})$aryl or $(C_7-C_{21})$alkylaryl, and pharmaceutically-acceptable salts thereof.

Also provided herein is an anti-viral composition, comprising an anti-viral effective amount of the above compound.

This invention also relates to an in vitro method of inhibiting the growth of a virus in a mammalian cell comprising contacting the cell with an anti-viral effective amount of the above compound under cell growth promoting conditions for a period of time effective to attain the desired effect.

Also part of this invention is a method of inhibiting the growth of a virus in a subject's cells comprising administering to the subject an anti-viral effective amount of the above compound for a period of time effective to attain the desired effect.

Still part of this invention is an in vitro method of inhibiting the growth of the HIV-1 virus in a mammalian cell comprising contacting the cell with an anti-HIV-1 effective amount of a compound of the chemical formula

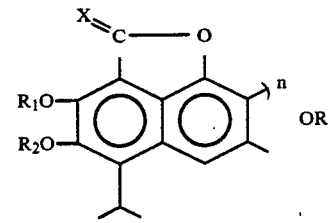

wherein
n is 1 or 2;
X is NH or O;
$R_1$ and $R_2$ are independently of one another H, $(C_1-C_{12})$alkyl, $(C_2-C_{12})$alkenyl, $(C_2-C_{12})$alkynyl, $(C_2-C_{12})$acyl, $(C_6-C_{12})$aryl or $(C_7-C_{21})$alkylaryl;
$R^3$ is C≡N or $COR^5$, wherein $R^5$ is selected from the group consisting of H, $(C_1-C_{12})$ alkyl, alkenyl or alkynyl, HO, $NH_2$ and $(C_2-C_{12})$ alkoxy; and
$R^4$ is selected from the group consisting of $(C_1-C_{12})$ alkyl, alkenyl or alkynyl and $(C_2-C_{12})$ acyl, and salts thereof for a period of time effective to attain the desired effect.

Still encompassed by this invention is a method of inhibiting the growth of the HIV-1 virus in a subject's cells comprising administering to the subject an anti-HIV-1 effective amount of a compound of the chemical formula

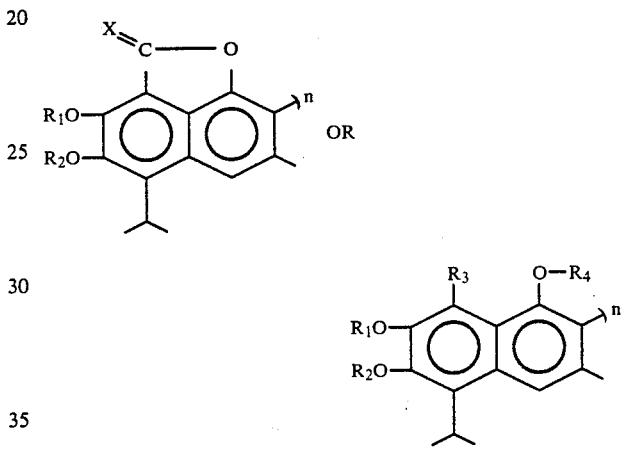

wherein
n is 1 or 2;
X is NH or O;
$R_1$ and $R_2$ are independently of one another H, $(C_1-C_{12})$alkyl, $(C_2-C_{12})$alkenyl, $(C_2-C_{12})$alkynyl, $(C_2-C_{12})$acyl, $(C_6-C_{12})$aryl or $(C_7-C_{21})$alkylaryl;
$R^3$ is C≡N or $COR^5$, wherein $R^5$ is selected from the group consisting of H, $(C_1-C_{12})$ alkyl, alkenyl or alkynyl, HO, $NH_2$ and $(C_2-C_{12})$ alkoxy; and
$R^4$ is selected from the group consisting of $(C_1-C_{12})$alkyl, alkenyl or alkynyl and $(C_2-C_{12})$ acyl, and salts thereof for a period of time effective to attain the desired effect.

A more complete appreciation of the invention and many of the attendant advantages thereof will be readily perceived as the same becomes better understood by reference to the following detailed description when considered in connection with the accompanying figures.

BRIEF DESCRIPTION OF THE DRAWINGS

FIG. 1-A represents the % IFA positive cells or anti-HIV activities (open bars) and the cytotoxicities of different concentrations of gossypol to MT4 cells (closed bars).

FIG. 1-B shows the % IFA positive cells or anti-HIV activities (open bars) and cytotoxicities of different concentrations of gossylic iminolactone to MT4 cells (closed bars).

FIG. 1-C shows the % IFA positive cells or anti-HIV activities (open bars) and cytotoxicities of different

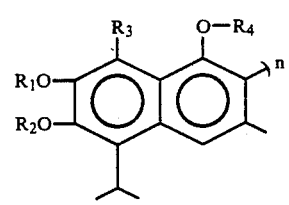

concentrations of gossylic nitrile-1,1'-diacetate to MT4 cells (closed bars).

FIG. 1-D shows the % IFA positive cells or anti-HIV activities (open bars) and cytotoxicities of different concentrations of gossylic lactone to MT4 cells (closed bars).

The above % IFA positive cells were determined 6 days after addition of HIV-1 virus. Cell viability is % viable cells relative to mock-treated cells or controls. FIGS. 1-A through D show one of many representative set of data.

Other objects, advantages and features of the present invention will become apparent to those skilled in the art from the following discussion.

BEST MODE FOR CARRYING OUT THE INVENTION

This invention arose from the desire of the inventors to provide novel anti-viral compounds which exhibit a tolerable toxicity to virus-infected patients. Moreover, the inventors desired to improve over prior art technology such as that represented by the compound AZT by providing drugs which interfere with the growth of viruses such as the HIV-1 virus via a mechanism other than the one utilized by AZT.

The present compounds represent one such group. These compounds may be utilized by themselves and, because of their different mechanism of action, may also be administered in combination with AZT and/or other anti-viral agents.

The present compounds have been shown to have substantial inhibiting activities against viruses such as the HIV-1 virus, the herpes simplex II virus and the influenza A virus. However, these are but mere examples of the scope of their anti-viral activities. In fact, the present compounds are active in the inhibition of growth of many enveloped viruses, with the HIV viruses belonging to this category.

Of particular importance is the fact that the present group of anti-viral agents are active at lower concentrations than gossypol and are toxic at concentrations substantially higher than their active concentrations.

Gossypol is known to bind tightly to the billirubin binding site of the protein albumin (Royer, R. E. et al, FEBS Letter 157: 28-30 (1983)). This property is not observed with known derivatives of gossypol (Royer, R. E. et al, J. Pharm. Sci. 77: 237-240, (1988)). The binding of gossypol to the protein albumin in blood has previously been implicated in the masking of its toxic properties (Haspel, H. C. et al, J. Pharmacol. Exp. Therap. 229: 218-225 (1984)) Thus, the toxicity of gossypol can be assumed to be for all practical purposes even greater than that observed in FIG. 1-A. And consequently, when the ratio of the active concentrations of the novel anti-viral agents to their toxicities is compared to those of gossypol, it is apparent that the novel compounds are extremely advantageous over the parent compound as well as AZT. In fact, the ratio of active concentration to toxic concentration for the present compounds is substantially higher than the same ratio for gossypol.

The compounds of this invention are gossypol or hemigossypol derivatives from which, inter alia, the aldehyde groups of the gossypol or hemigossypol molecule have been removed to effect a reduction in their toxicities.

The novel compounds of the invention have the chemical formula

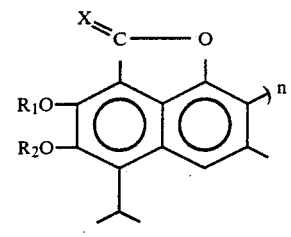

wherein n is 1 or 2;

X is selected from the group consisting of NH and O; and $R_1$ and $R_2$ are independently of one another H, ($C_1$–$C_{12}$)alkyl, ($C_2$–$C_{12}$)alkenyl, ($C_2$–$C_{12}$)alkynyl ($C_2$$C_{12}$)acyl ($C_6$–$C_{12}$)aryl or ($C_7$–$C_{21}$)alkylaryl, and pharmaceutically-acceptable salts thereof.

A particularly preferred group of compounds is that wherein X is NH. Another preferred group is that where the nitrile compound is in the form of a pharmaceutically-acceptable salt. Typically, salts of the nitrile derivative may be any pharmaceutically-acceptable salts such as acetate, gluconate, and the like. However, other salts known in the art as being pharmaceutically-acceptable are also within the scope of this invention.

Still another preferred group of the present compounds is that wherein X is O. This lactone may also be present in the form of a salt if the $R_1$ and/or $R_2$ substituents are acidic such as is the case of H.

Another preferred group of compounds is that wherein n is 2, which corresponds to the gossypol family of compounds.

Yet another preferred group of compounds is that wherein both $R_1$ and $R_2$ are H as well as their pharmaceutically-acceptable salts. Compounds representative of this group are exemplified herein.

Another preferred group of compounds of this invention is that wherein $R_1$ and $R_2$ are alkyl such as methyl, ethyl and the like.

Some of the compounds prepared by the inventors are shown below.

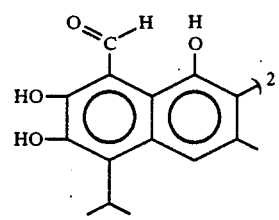

I

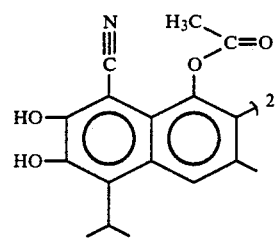

II

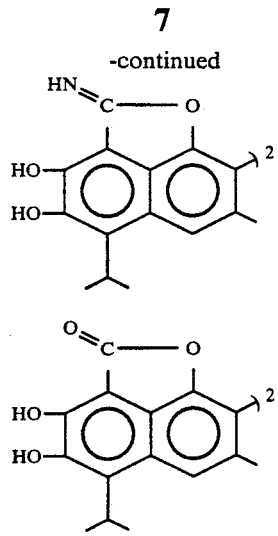

Gossylic iminolactones (derivatives of Compound III) can be prepared by reacting 1,1'-diacylated gossylic nitriles or 1,1',6,6',7,7'-hexaacylated gossylic nitrile, such as those described in U.S. Pat. No. 4,806,568, in concentrated acid at low temperature. Typically, this reaction may be conducted on ice or at a temperature of about 0° to 5° C. with stirring until the mixture is homogenized. The reaction mixture may then be allowed to stand at room temperature, cooled again and allowed to proceed until a solid precipitate is observed. This precipitate can be separated from the supernate and recrystalized from a solvent such as is known in the art. Further purification of the compound may be attained by further recrystallization and purification techniques known in the art which need not be described further herein.

Gossylic lactones (derivatives of Compound IV) may be prepared from the gossylic immunolactones (derivatives of Compound III) by dissolving the latter compounds in a solvent such as 95% ethanol in the presence of an acid. The reaction may be allowed to proceed at reflux and then cooled to about 0° to 5° C. A precipitate may then be separated from the supernate and further purified by recrystallization or other means as described above.

This invention also provides the novel compounds in an anti-viral composition which comprises an anti-viral effective amount of the compound of the chemical formula

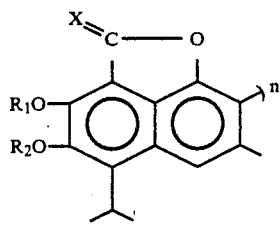

wherein
n is 1 or 2;
X is selected from the group consisting of NH and O; and
$R_1$ and $R_2$ are independently of one another H, ($C_1$–$C_{12}$)alkyl, ($C_2$–$C_{12}$)alkenyl, ($C_2$–$C_{12}$)alkynyl, ($C_2$–$C_{12}$)acyl, ($C_6$–$C_{12}$)aryl or ($C_7$–$C_{21}$)alkylaryl, and pharmaceutically-acceptable salts thereof.

The novel compounds may be present in the composition in varying amounts, typically about 0.1 to 99.9 wt. % thereof, more preferably about 0.5 to 90 wt. %, still more preferably about 1 to 80 wt. % and even more preferably about 1 to 50 wt. % of the composition.

For use as therapeutic agents, the novel compounds may be used alone or in combination with various pharmaceutically-acceptable carriers. Typical carriers are known in the art and need not be further described herein.

The novel compounds described herein may be utilized in an in vitro method of inhibiting the growth of a virus in a mammalian cell by contacting the cell with an anti-viral effective amount of the compound of the chemical formula

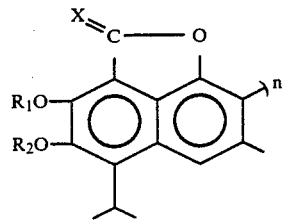

wherein n is 1 or 2, X selected from the group consisting of NH and O, and $R_1$ and $R_2$ are independently of one another H, ($C_1$–$C_{12}$)alkyl, ($C_2$–$C_{12}$)alkenyl, ($C_2$–$C_{12}$)alkynyl ($C_2$–$C_{12}$)acyl, ($C_6$–$C_{12}$)aryl or ($C_7$–$C_{21}$)alkylaryl, and pharmaceutically-acceptable salts thereof, under cell growth promoting conditions for a time effective to attain the desired effect.

Typically, the concentration of the compound in the medium may be about 1 to 100 uM and more preferably about 1 to 10 uM. In general, these concentrations show low toxicity to the cells. The time of contact may vary between about 1 hour and 6 days, and may exceed 6 days.

In a preferred application of the above method the cell to which the compound is applied is a human cell.

Also provided herein is a method of inhibiting the growth of a virus in a subject is cells comprising administering to the subject an anti-viral effective amount of the compound of the chemical formula

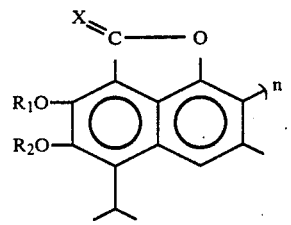

wherein n is 1 or 2, X is selected from the group consisting of NH and O, and $R_1$ and $R_2$ are independently of one another H, ($C_1$–$C_{12}$)alkyl, ($C_2$–$C_{12}$)alkenyl, ($C_2$–$C_{12}$)alkynyl ($C_2$–$C_{12}$)acyl, ($C_6$–$C_{12}$)aryl or ($C_7$–$C_{21}$)alkylaryl, and pharmaceutically-acceptable salts thereof for a period of time effective to attain the desired effect.

Typically, the novel compounds of the invention are administered as anti-viral agents to mammals in amounts of about 30 to 60 mg per day, and more preferably about 15 to 30 mg per day. Depending on the route of administration this dosage regimen may be adjusted to provide an optimum therapeutic response which also takes into account the physical condition being treated. By means of example, more than one dose may be administered daily, each one having a reduced content of the compound when compared with a single daily dose.

The novel compounds may be administered by oral, intravenous, intramuscular or subcutaneous routes. Whenever possible the oral route is preferred.

For oral administration, the compounds may be compounded with an inert diluent or with an edible carrier, they may be enclosed in gelled capsules, compressed into tablets or incorporated in the diet. Other excipients may be added to the formulation such as those utilized for ingestible tablets, troches, capsules, elixers, suspensions, syrups and wafers, among others. Also contained in the preparation may be a binder such as gum tragacanth, acacia, corn starch or gelatin, excipients such as dicalcium phosphate, disintegrating agents such as corn starch, potatoe starch, alginic acid and the like, lubricants such as magnesium sterate, sweetening agents such as sucrose, lactose or saccharin, flavoring agents such as peppermint, olive, wintergreen or cherry flavoring as well as other known additives. A liquid carrier may also be added to the capsules.

Coatings or otherwise modified forms of the preparation are also contemplated herein such as coatings of shellac, sugar and the like.

A syrup or elixir may contain the novel compound, succhrose as a sweetening agent, methyl or propyl parabens as preservatives, a dye and a flavoring such as cherry or orange flavors, among others. Any material added to the pharmaceutical composition should be pharmaceutically-acceptable and substantially non-toxic in the amounts employed. Sustained-release preparations and formulations are also within the confines of this invention.

The present compounds may also be administered by the intraperitoneal and perenteral routes. Solutions of the active compound as a free acid or a pharmaceutically-acceptable salt may be administered in water with or without a surfactant such as hydroxypropyl cellulose. Dispersions are also contemplated such as those utilizing glycerol, liquid polyethylene glycols and mixtures thereof and oils. Antimicrobial compounds may also be added to the preparations. Injectable preparations may include sterile aqueous solutions or dispersions and powders which may be diluted or suspended in a sterile environment prior to use. Carriers such as solvents or dispersion media containing, e.g., water, ethanol polyols, vegetable oils and the like, may also be added. Coatings such as lecithin and surfactants may be utilized to maintain the proper fluidity of the composition. Isotonic agents such as sugars or sodium chloride may also be added as well as products intended for the delay of absorption of the active compounds such as aluminum monostearate and geletin. Sterile injectable solutions are prepared as is known in the art and filtered prior to storage and/or administration. Sterile powders may be vacuum dried or freeze dried from a solution or suspension containing them.

Pharmaceutically-acceptable carriers as utilized in the context of this patent include any and all solvents, dispersion media, coatings, antimicrobial agents, isotonic and absorption delaying agents and the like as is known in the art. All preparations are prepared in dosage unit forms for uniform dosage and ease of administration. Each dosage unit form contains a predetermined quantity of active ingredient calculated to produce a desired therapeutic effect in association with a required amount of pharmaceutical carrier.

Also provided herein is an in vitro method of inhibiting the growth of the HIV-1 virus in a mammalian cell comprising contacting the cell with an anti-HIV-1 effective amount of that compound of the chemical formula

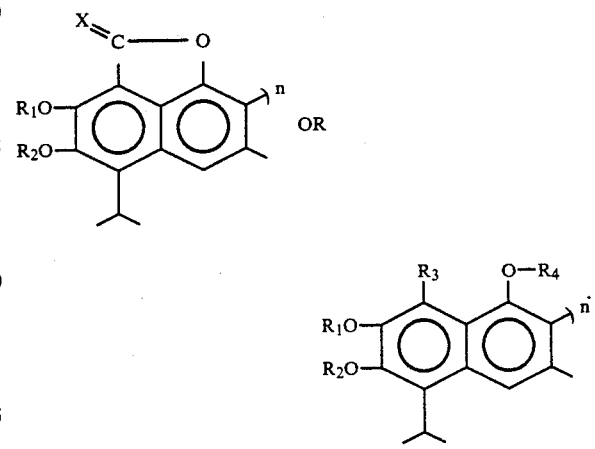

wherein
n is 1 or 2, X if NH or O, $R_1$ and $R_2$ are independently of one another $H_1(C_1-C_{12})$alkyl, $(C_2-C_{12})$alkenyl, $(C_2-C_{12})$alkynyl, $(C_2-C_{12})$acyl, $(C_6-C_{12})$aryl or $(C_7-C_{21})$alkylaryl, $R^3$ is $C\equiv N$ or $COR^5$, wherein $R^5$ is selected from the group consisting of H, $(C_1-C_{12})$ alkyl, alkenyl or alkynyl, HO, $NH_2$ and $(C_2-C_{12})$ alkoxy; and $R^4$ is selected from the group consisting of $(C_1-C_{12})$ alkyl, alkenyl or alkynyl and $(C_2-C_{12})$ acyl, and pharmaceutically-acceptable salts thereof, for a period of time effective to attain the desired effect.

The above group of compounds encompasses the novel compounds provided herein as well as compounds disclosed by the inventors in U.S. Pat. No. 4,806,568. The inhibition of the growth of the HIV-1 virus is a novel application that the inventors have unexpectedly found of previously known compounds. The mammalian cells which can be treated by the present method include human cells.

Typically, the compounds are contacted with the cells at a concentration of about 1 to 100 uM and preferably about 1 to 10 uM.

Also provided herein is a method of inhibiting the growth of the HIV-1 virus in a subject comprising administering to the subject an anti-HIV-1 effective amount of a compound of the chemical formula

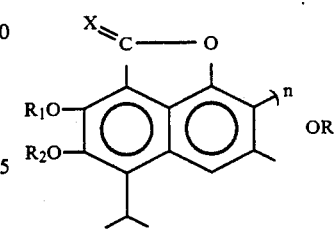

-continued

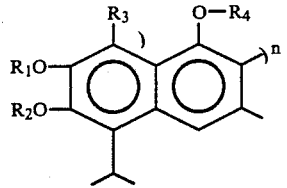

wherein
n is 1 or 2, X if NH or O, $R_1$ and $R_2$ are independently of one another H, $(C_1-C_{12})$alkyl, $(C_2-C_{12})$alkenyl, $(C_2-C_{12})$alkynyl, $(C_2-C_{12})$acyl, $(C_6-C_{12})$aryl or $(C_7-C_{21})$alkylaryl;
$R^3$ is C≡N or $COR^5$, wherein $R^5$ is selected from the group consisting of H, $(C_1-C_{12})$ alkyl, alkenyl or alkynyl, HO, $NH_2$ and $(C_2-C_{12})$ alkoxy; and
$R^4$ is selected from the group consisting of $(C_1-C_{12})$ alkyl, alkenyl or alkynyl and $(C_2-C_{12})$ acyl, and pharmaceutically-acceptable salts thereof, for a period of time effective to attain the desired effect.

The novel compounds have been shown active in the inhibition of enveloped viruses such as HIV-1, herpes simplex II and influenza A viruses.

The methods of this invention may be applied to mammalian subjects including human subjects. Typically, the amount of the compound administered to the subject is about 30 to 60 mg/day, preferably about 15 to 30 mg/day. The compounds may be administered to a patient for a period of about 6 to 12 days, and in some cases a period in excess of 12 days.

Having now generally described this invention the same will be better understood by reference to certain specific examples, which are included herein for purposes of illustration only and are not intended to be limiting of the invention or any embodiment thereof, unless so specified.

EXAMPLES

Example 1 Synthesis of gossylic iminolactone (Compound III).

Gossylic 1,1'-diacetate (0.5 g, 0.84 mmol) was stirred into 5 ml of concentrated sulfuric acid which had been chilled to 0° to 5° C. in an ice bath. Stirring was continued until the mixture was homogeneous. The reaction mixture was then allowed to stand for 30 minutes at room temperature. Ice (50 g) was added to the mixture with stirring and stirring was continued until the ice melted.

The precipitated solid was filtered off and recrystallized from acetonitrile to give 0.3 g (0.59 mmol, 70%) of III as red microcrystalline needles which decomposed above 300° C. without melting.

NMR (perdeuterodioxane): 1.52 (d, 12 H, J=7 Hz), 2.30 (s, 6 H), 3.65 (septet, 2 H, J=7 Hz), 6.99 broad s, 6 H), 7.60 (s, 2 H).

Example 2: Synthesis of derivatives of gossylic iminolactone.

Derivatives of Compound III within the scope of this invention may also be synthesized by applying the above procedure to any of the other 1,1'-diacylated gossylic nitriles or 1,1',6,6',7,7'-hexaacylated gossylic nitriles described in U.S. Pat. No. 4,806,568.

Example 3: Synthesis of gossylic lactone (Compound IV).

Compound III (50 mg, 0.098 mmol) was refluxed in 5 ml of 95% ethanol and 1 ml of 6 M HCl and was poured onto 50 g of ice. The precipitate was filtered off as soon as the ice melted to give 45 mg (0.087 mmol, 89%) of IV. This material was crystallized from toluene to give tan microcrystalline material which decomposed without melting.

NMR ($CDCl_3$): 1.55 (d, 14 H, J=7 Hz), 2.34 (s, 6 H), 3.88 (septet, 2 H, J=7 Hz, 6.3 (broad s, 2 H), 7.7 (s, 2 H).

Example 4: Synthesis of derivatives of gossylic lactone.

Derivatives of Compound IV within the scope of the invention may be synthesized by applying the procedure of Example 3 to the corresponding derivative of Compound III.

Example 5: Compound III - Structure Determination.

In addition to the spectral data provided in Example 1 evidence for the structures of compounds III and IV consists of the following.

The structure of III is supported by the facile conversion of III to IV in dilute acid. An imino group would be expected to be hydrolyzed under these conditions. When compound III is treated with benzoyl chloride prior to acid hydrolysis, one of the hydrolysis products is benzamide which is what would be expected for the iminolactone structure.

Example 6: Compound IV - Structure Determination.

In order to confirm the structure of compound IV, this compound was treated with dimethyl sulfate in base to produce tetramethylgossylic lactone which has been previously reported (R. Adams and T. A. Geissman, J. Am. Chem. Soc. 60: 2166 (1938)). Spectral data are provided in Example 2 above.

Example 7: Materials for Tests of Activity and Toxicity.

Drugs

Gossypol (I), as the acetic acid complex, was obtained from the Southern Regional Research Center, U.S.D.A. (New Orleans, La.).

Gossylic nitrile-1,1'-diacetate (II) was synthesized from gossypol dioxime by treatment of the dioxime with acetic anhydride and sodium acetate as described previously (U.S. Pat. No. 4,806,568).

Gossylic iminolactone (III) and gossylic lactone (IV) were synthesized from II.

Virus

An LAV-A isolate of human immunodeficiency virus (HIV-1) was used in this study. LAV-A was originally isolated by Dr. L. Montagnier, Pasteur Institute, Paris, and was obtained from Dr. T. Folks, NIAID.

Example 8: Test for Anti-viral Activities of Compounds I, II, III and IV Against the HIV-1 virus.

MT4 cells, $10^7$ cells/ml, were infected for 1 hour at 4° C., with stock HIV-1 virus, 0.5 ml stock/$10^7$ cells. The stock HIV-1 virus had a titer greater than 2.0 OD units/0.2 ml in the DuPont p24 ELISA assay.

The infected cells were then resuspended in a complete medium (RPMI 1640 with 20% FBS, L-glutamine, 2 mM, penicillin, 100 units/ml, and streptomycin, 100 ug/ml). Aliquots were added to 24-well tissue culture plates containing varying concentrations of Compounds I, II, III and IV in complete media. The final cell concentration was $1.5 \times 10^5$ cells/ml.

Positive control wells received no drug. Negative control wells received mock-treated MT4 cells. Cells were incubated at 37° C. in 5% $CO_2$. Media was changed after 3 days with fresh complete media containing the appropriate drug.

After 6 days, the viability of the MT4 cells, control or infected, was determined by trypan blue exclusion, which is a standard procedure to determine cell viability.

The percent HIV-1 viral infection was determined by an immunofluorescence assay (IFA) using heat-inactivated, pooled human anti-sera from HIV-positive patients as the first antibody and goat anti-human IgG conjugated with FITC as the second antibody. This is a standard immunoassay known in the art.

Slides were counterstained with Evans blue to obtain total cell counts from the same slides as is known in the art. Uninfected cells were consistently negative for fluorescence.

Example 9: Results of Test for Anti-viral Activities of Compounds I, II, III and IV against the HIV-1 virus.

The antiviral activity of gossypol (Comp. I) against HIV-infected MT4 cells is shown in FIG. 1A (open bars). Gossypol at 1 uM concentration inhibited virus replication approximately 50%. However, 1 uM gossypol exhibited significant toxicity to the host cell, as shown in FIG. 1A (closed bars). This host cell toxicity of goddypol masked any clear demonstration of antiviral activity.

The antiviral activity of gossylic iminolactone (Comp. III) against HIV-infected MT4 cells is shown in FIG. 1B (open bars). Gossylic iminolactone, like gossypol, inhibited virus replication approximately 50% at 1 uM drug concentration. Unlike gossypol, however, gossylic iminolactone showed no toxicity to the host cell until the drug concentration reached 50 uM FIG. 1B, closed bars). Based upon a cytotoxic dose ($CD_{50}$) between 25 uM and 50 uM, and an $ED_{50}$ of 1 uM, the selectivity index ($CD_{50}/ED_{50}$) is calculated to be between 25 and 50 for gossylic iminolactone.

The antiviral activity of gossylic nitrile-1,1'-diacetate (Comp. II) is shown in FIG. 1C (open bars). This derivative inhibited virus replication by approximately 50% at 50 uM concentration of drug, whereas toxicity was demonstrated at 250 uM concentration.

The antiviral activity of gossylic lactone (Comp. IV) is shown in FIG. 1D (open bars). This derivative of gossypol exhibited very little antiviral activity below 250 uM, where there was pronounced toxicity to the MT4 cell.

The invention now being fully described, it will be apparent to one of ordinary skill in the art that many changes and modifications can be made thereto without departing from the spirit or scope of the invention as set forth herein.

What is claimed is:

1. A compound of the chemical formula

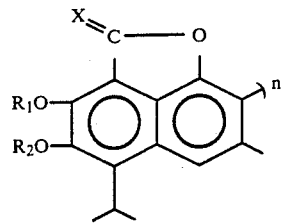

wherein
n is 1 or 2:
X is NH; and
$R_1$ and $R_2$ are independently of one another H, $(C_1-C_{12})$alkyl $(C_2-C_{12})$alkenyl, $(C_2-C_{12})$alkynyl, $(C_2-C_{12})$acyl, $(C_6-C_{12})$aryl or $(C_7-C_{21})$alkylaryl, or a pharmaceutically-acceptable salt thereof.

2. A compound of the chemical formula

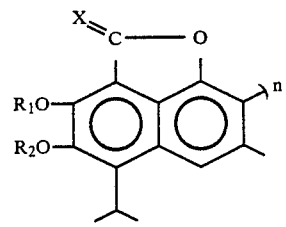

n is 1 or 2;
X is O; and
$R_1$ and $R_2$ are independently of one another H, $(C_2-C_{12})$alkynyl, $(C_2-C_{12})$acyl, $(C_6-C_{12})$aryl or $(C_7-C_{21})$alkylaryl, or a pharmaceutically-acceptable salt thereof.

3. The compound of claim 1, wherein n is 2.

4. The compound of claim 1, wherein $R_1$ and $R_2$ are H.

5. An anti-viral composition, comprising an anti-viral effective amount of the compound of claim 1 and a pharmaceutically acceptable inert carrier.

6. The anti-viral composition of claim 4, wherein the compound is present in an amount of about 0.1 to 99 wt. % of the composition.

7. An in vitro method of inhibiting the growth of a virus in a mammalian cell comprising contacting the cell with an anti-viral effective amount of the composition of claim 5 under cell growth promoting conditions, for a period of time effective to attain the desired effect.

8. The method of claim 7, wherein the cell is a human cell.

9. A method of inhibiting the growth of a virus in a subject's cells comprising administering to the subject an amount of the composition of claim 5 comprising an anti-viral effective amount of the compound for a period of time effective to attain the desired effect.

10. The method of claim 9, wherein the virus is selected from the group consisting of enveloped viruses.

11. The method of claim 9, wherein the subject is a human subject.

12. The method of claim 11, wherein the antiviral effective amount of the compound is about 30 to 60 mg/day.

* * * * *

UNITED STATES PATENT AND TRADEMARK OFFICE
CERTIFICATE OF CORRECTION

PATENT NO. : 5,026,726
DATED : June 25, 1991
INVENTOR(S) : David L. Vander Jagt, et. al.

It is certified that error appears in the above-indentified patent and that said Letters Patent is hereby corrected as shown below:

On the Title page, item [75], inventor: change David L. Jagt to --David L. Vander Jagt--.
On the Title page, item [57], line 3 should read as follows:
--wherein n is 1 or 2, X is NH or o, and $R_1$ and $R_2$ are--.
Column 6, line 46, after "compounds" insert --discussed or--;
Column 7, line 38, change "immuno" to --imino--;
Column 9, line 29, change "succhrose" to --sucrose--; and
Column 13, line 34, change "goddypol" to --fossypol--.
Column 14, lines 17 and 34, change "$(C_7-C2_1)$" to --$C_7-C_{21}$)--.

Signed and Sealed this

Seventeenth Day of May, 1994

BRUCE LEHMAN

Attest:

Attesting Officer

Commissioner of Patents and Trademarks